(12) United States Patent
Schulze-Trautmann et al.

(10) Patent No.: US 9,347,007 B2
(45) Date of Patent: May 24, 2016

(54) MICROCRYSTALLINE PARAFFIN, METHOD FOR PRODUCING MICROCRYSTALLINE PARAFFINS, AND USE OF THE MICROCRYSTALLINE PARAFFINS

(75) Inventors: Helmuth Schulze-Trautmann, Hamburg (DE); Michael Matthäi, Henstedt-Ulzburg (DE); Thorsten Butz, Buchholz (DE); Günter Hildebrand, Rehmsdorf (DE)

(73) Assignee: SASOL WAX GMBH, Hamburg (DE)

( * ) Notice: Subject to any disclaimer, the term of this patent is extended or adjusted under 35 U.S.C. 154(b) by 1082 days.

(21) Appl. No.: 10/516,672

(22) PCT Filed: May 19, 2003

(86) PCT No.: PCT/EP03/05236
§ 371 (c)(1),
(2), (4) Date: Aug. 8, 2005

(87) PCT Pub. No.: WO03/102115
PCT Pub. Date: Dec. 11, 2003

(65) Prior Publication Data
US 2006/0118462 A1 Jun. 8, 2006

(30) Foreign Application Priority Data
Aug. 13, 2002 (DE) ................................. 102 37 651
Dec. 2, 2002 (DE) ................................. 102 56 431

(51) Int. Cl.
*C10G 45/62* (2006.01)
*C10G 45/64* (2006.01)
*C10G 73/44* (2006.01)

(52) U.S. Cl.
CPC ..................................... *C10G 73/44* (2013.01)

(58) Field of Classification Search
CPC ................................. C10G 45/62; C10G 45/64

USPC .......................................... 208/14, 20, 24, 27
See application file for complete search history.

(56) References Cited

U.S. PATENT DOCUMENTS

| 2,668,866 A * | 2/1954 | Good et al. ................... 585/751 |
| 4,419,220 A | 12/1983 | LaPierre et al. |
| 5,904,834 A | 5/1999 | Leenhouts |
| 5,981,419 A * | 11/1999 | Carati et al. .................... 502/66 |
| 7,169,726 B2 | 1/2007 | John et al. |
| 7,875,166 B2 | 1/2011 | Matthai et al. |
| 2004/0199040 A1* | 10/2004 | Hoek et al. .................... 585/664 |

FOREIGN PATENT DOCUMENTS

| DE | 101 26 516 | 12/2002 |
| EP | 0 435 619 | 7/1991 |
| EP | 582347 A1 * | 2/1994 |
| EP | 668342 A1 * | 8/1995 |
| EP | 776959 A2 * | 6/1997 |
| WO | WO 01 74969 | 10/2001 |
| WO | WO 0174969 A2 * | 10/2001 |

OTHER PUBLICATIONS

Office Action mailed on Jul. 29, 2008 corresponding to U.S. Appl. No. 10/477,910.
Response filed on Jan. 29, 2009 corresponding to U.S. Appl. No. 10/477,910.

* cited by examiner

*Primary Examiner* — Randy Boyer
(74) *Attorney, Agent, or Firm* — Lucas & Mercanti, LLP; Klaus P. Stoffel

(57) ABSTRACT

Microcrystalline paraffin having a consistency in a rage of paste-like to solid, prepared by catalytic hydroisomerization of FT paraffins having a carbon chain length distribution in a range of 20 to 105 at temperatures above 200° C., and being free of aromatic compounds, heterocyclic compounds, and naphthenes.

17 Claims, 3 Drawing Sheets

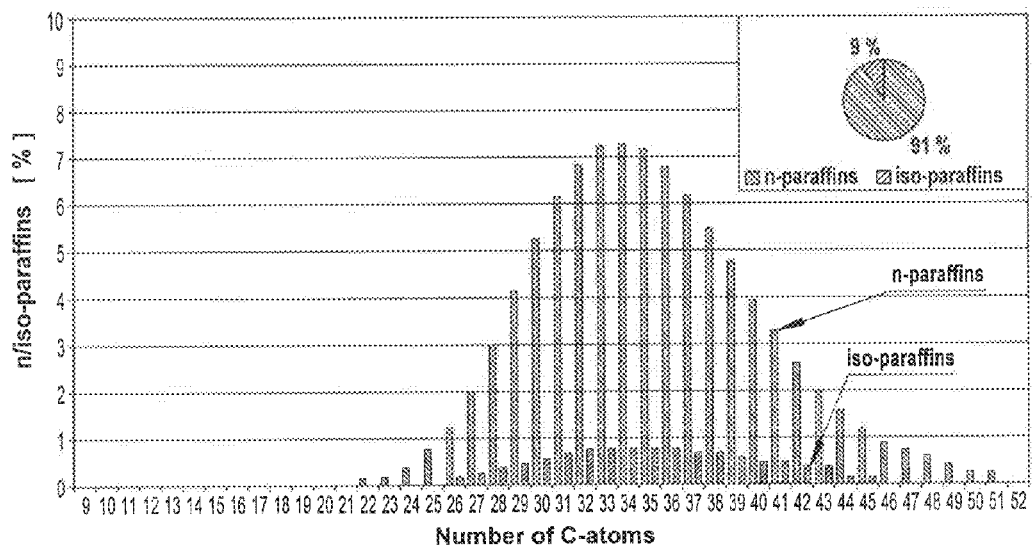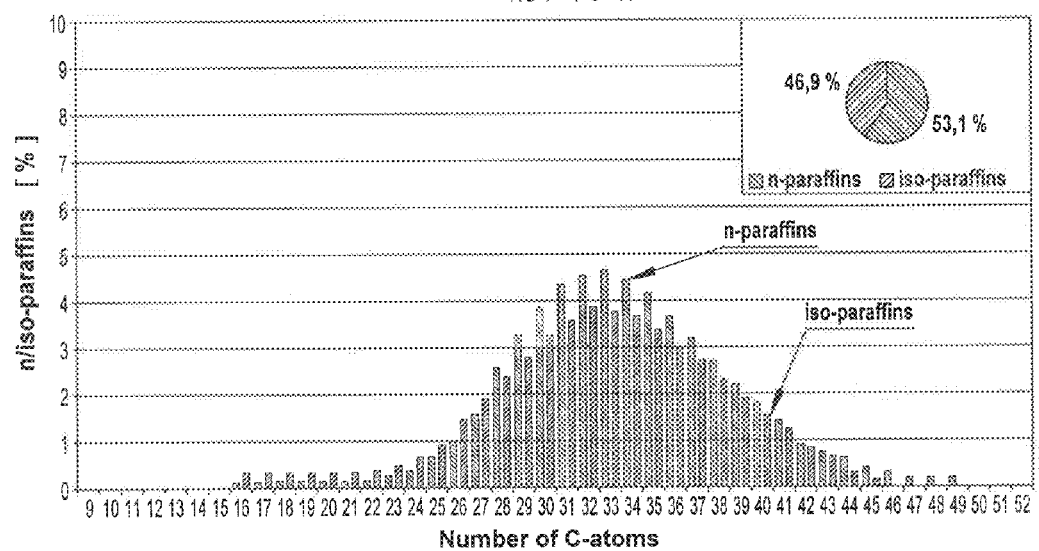

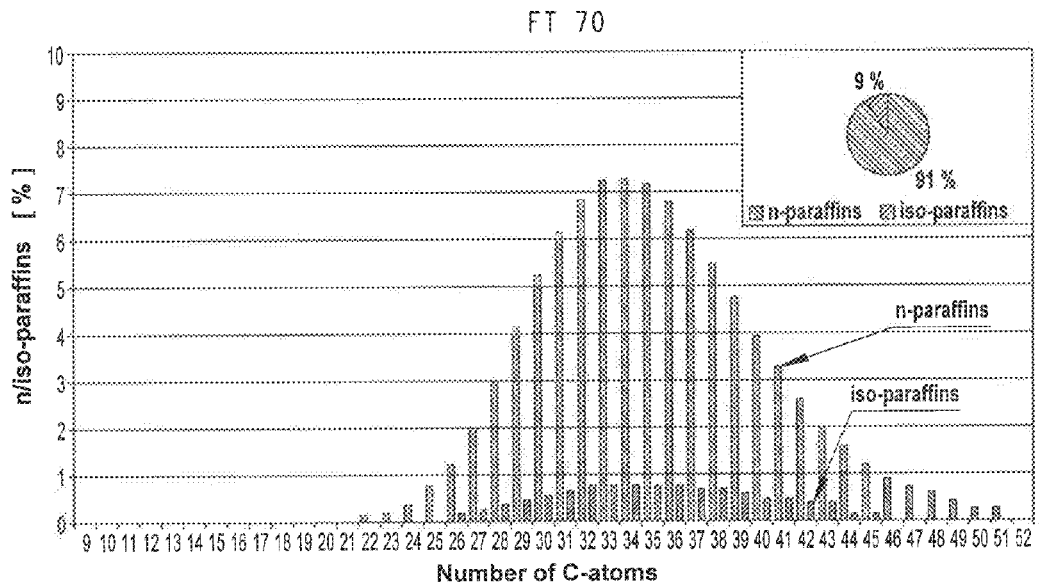
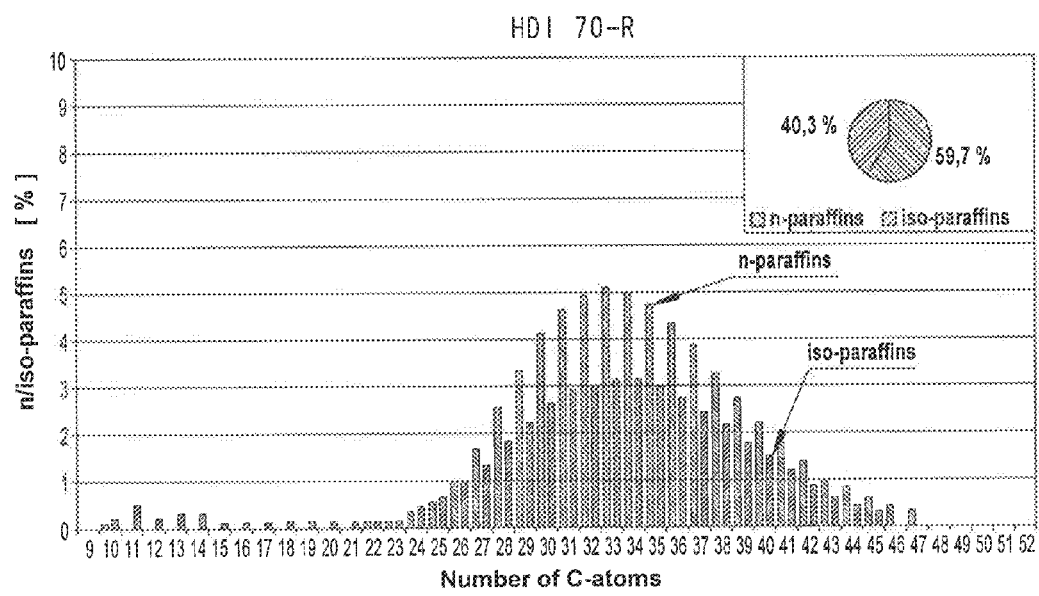

MICROCRYSTALLINE PARAFFIN, METHOD FOR PRODUCING MICROCRYSTALLINE PARAFFINS, AND USE OF THE MICROCRYSTALLINE PARAFFINS

CROSS-REFERENCE TO RELATED APPLICATIONS

This patent application claims the benefit of priority of German Patent Application No. 10237651.4, tiled Aug. 13, 2001, German Patent Application No. 10256431.0, filed Dec. 2, 2001 and PCT/EP02/05970, filed May 31, 2001.

The invention relates to a microcrystalline paraffin, its preparation and its use.

Conventional microcrystalline paraffin obtained from petroleum (also known as microwaxes) consists of a mixture of saturated hydrocarbons which are solid at room temperature and have a chain length distribution from $C_{25}$ to $C_{80}$. The microcrystalline paraffins comprise n-alkanes and frequently branched isoalkanes and alkyl-substituted cycloalkanes (naphthenes) and also, even if generally only in small proportions, aromatics. The content of isoalkanes and of naphthenes ranges from 40 to 70%, determined by the EWF Standard Test Method for analysis of hydrocarbon wax by gas chromatography. The dominance in terms of quantity of the isoalkanes (and the naphthenes) determines their microcrystalline structure.

The solidification range is between 50 and 100° C. in accordance with DIN ISO 2207. The needle penetration test gives values between $2\times10^{-1}$ and $160\times10^{-1}$ mm in accordance with DIN 51579. The solidification point and the needle penetration are used to distinguish, among the microcrystalline paraffins, between plastic and hard microcrystalline paraffins. Soft plastic 30 microcrystalline: paraffins (known as petrolates) are tacky with a strongly pronounced adhesive capability and have solidification points from 65 to 70° C. and penetration values from 45 to $160\times10^{-1}$ mm. The oil contents are in the range between 1 and 15%. Plastic 35 microcrystalline paraffins are readily shapeable and kneadable and have solidification points between 65 and 80° C. and penetration values from 10 to $30\times10^{-1}$ mm. The oil contents can be up to 5%. Hard microcrystalline paraffins are hard and tough and slightly adhesive with solidification points from 80 to 95° C. and penetration values from 2 to $15\times10^{-1}$ mm. The oil contents are not more than 2% (see Ullmanns Encyclopedia of Industrial Chemistry, VCH-Verlagsgesellschaft 1996).

Microcrystalline paraffins have a high molar mass and thus high boiling points. They have in the past been obtained from the residues of vacuum distillation of petroleum and from precipitates of petroleum formed during its storage (bottom residue, residual wax) using technologically very complicated and costly processes having a plurality of stages, for example deasphalting, solvent extraction, deparaffination, deoiling and refining. The deoiled microcrystalline paraffins contain sulfur, nitrogen and oxygen compounds as impurities. They are therefore not completely odorless and have a dark yellow to dark brown color. The refining which is therefore necessary is carried out as a function of the later use by bleaching (industrial applications) or by hydrorefining (applications in the food and pharmaceutical industries).

Microcrystalline paraffins are used predominantly as mixing components in paraffin and wax mixtures. The amount used is usually in the ranges up to 5%. They are employed, in particular, to increase the hardness and melting point of these mixtures and also to improve flexibility and oil binding capacity. Typical applications are, for example, the production of waxes for impregnation, coating and lamination for the packaging and textile industries, of heat sealing compounds and hot melt adhesives and also of pharmaceutical and cosmetic products, including chewing gum. Furthermore, they are used in embedding compounds and cable insulation compounds, as well as generally in plastics, and also in the candle, rubber and tire industries, as well as in cleaning, antiskid and corrosion protection products.

It is known from WO 01/74971 that a Fischer-Tropsch product which has a broad boiling range and also contains proportions of liquid product can be isomerized under mild conditions and a wax can be isolated from the liquid hydroisomerizate by distilling off the lighter fractions. The hydrogenation temperature is given as a range from 204 to 343° C. (however: 348° C. in example), but the lower temperature range which is not supported by examples appears questionable in terms of its ability to be implemented. The high-boiling fractions of the starting material are blended with the wax which has been obtained in this way. A cobalt-molybdenum catalyst on aluminosilicate is reported as typical catalyst. Zeolites mentioned as being suitable are zeolite Y or ultrastable zeolite Y. The fact that an additional process step, viz. distillation, has to be employed in this proposal appears to be a disadvantage since it makes the production of the soft microcrystalline wax more expensive.

DE 69 418 388 T2 describes hydroisomerization of n-paraffins which have more than 15 carbon atoms and are solid at room temperature using a catalyst based on a metal of group VIII, in particular platinum, and a borosilicate which is isomorphous with beta-zeolite to give liquid products which are suitable for the production of lubricating oils.

DE 695 15 959 T2 describes the hydroisomerization of wax-containing starting materials to form liquid products which are suitable for the production of lubricating oils. A temperature from 270° to 360° C. and a pressure from 500 to 1500 psi or from 3.44 MPa to 10.36 MPa is employed here. The hydrogen is fed into the reactor at a rate of 1000 to 10 000 SCF/bbl and the wax is fed in at an LHSV of 0.1 to 10. The catalyst is based on a metal component on a porous, heat-resistant metal oxide support, in particular from 0.1 to 5% by weight of platinum on aluminum oxide or zeolites such as, for example, offretite, zeolite X, zeolite Y, ZSM-5, ZSM-2, etc. The starting material to be isomerized can be any wax or wax-containing material, such as, for example, slack waxes or Fischer-Tropsch wax. The isomerization product is liquid and serves as starting material for the production of lubricating oil components.

In light of this prior art, the invention addresses the object of providing a novel microcrystalline paraffin, a process for preparing it and a use of this microcrystalline paraffin.

This object is firstly and substantially achieved by the subject matter of claim 1 (product) or of claim 5 (process) or of claim 10 (use). The aim of this is that the microcrystalline paraffin which can be prepared by catalytic hydroisomerization at temperatures above 200° C., preferably 220 to 270° C., of paraffins obtained from the Fischer-Tropsch synthesis (FT paraffins) has a carbon chain length distribution in the range from $C_{20}$ to $C_{105}$. In contrast to natural microwaxes, such a microcrystalline paraffin is free of naphthenes and aromatics. Despite isomerization, crystallinity is retained. Continuous preparation with defined properties is made possible. The preparation can even be carried out in a single process step. A product to be referred to as a microwax, having a low and high solidification point range, is provided. Continuous or batchwise catalytic hydroisomerization of T paraffins can be carried out. With regard to FT paraffins per se, reference may be made, in particular, to the information provided by A. Kühnle in Fette. Seifen. Anstrichmittel, volume 84, pages 156 ff.

"Fischer-Tropsch Wachse Synthese, Struktur, Eigenschaften und Anwendungen". Stated briefly, FT paraffins are paraffins which have been prepared by the Fischer-Tropsch process in a known manner from synthesis gas (CO and H2) in the presence of a catalyst at elevated temperature. They represent the highest-boiling fraction of the hydrocarbon mixture. The products formed are basically long-chain alkanes which have little branching and are free of naphthenes and aromatics and of oxygen compounds and sulfur compounds.

Such FT paraffins having a high proportion of n-paraffins and a carbon chain length in the range from $C_{20}$ to $C_{105}$ are converted by the process described here into high-melting, microcrystalline paraffins having a high proportion of isoparaffins.

BRIEF DESCRIPTION OF THE DRAWINGS

FIG. 2 illustrates gas chromatograms of n-paraffin/iso-paraffin (%) verses the number of carbon atoms for FT70 (FT paraffin) and HDI 70A. respectively, of Example 2.

FIG. 3 illustrates gas chromatograms of n-paraffin/iso-paraffin (%) verses the number of carbon atoms for FT70 and HDI 70R, respectively, of Example 3.

Figure 1:
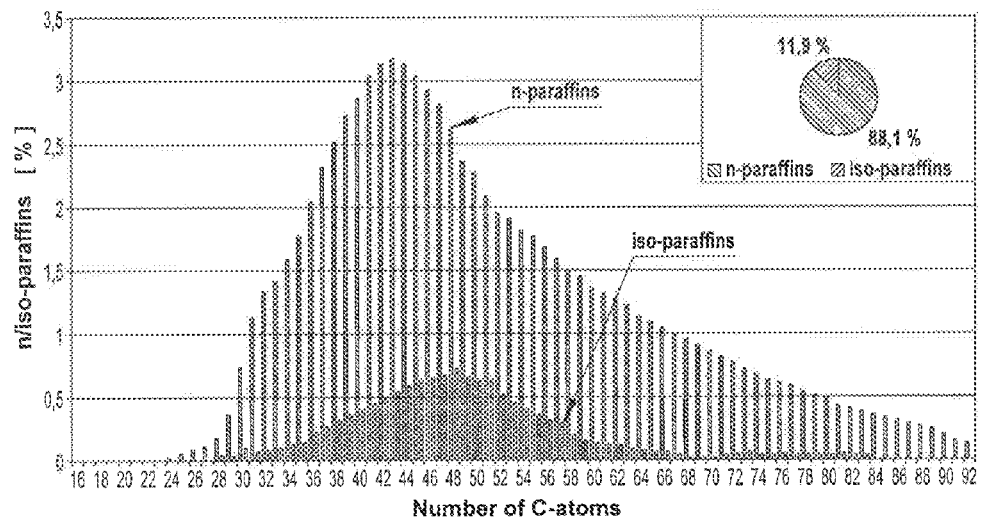
FIG. 1 illustrates gas chromatograms of n-paraffin/iso-paraffin (%) verses the number of carbon atoms for H 8 (FT paraffin) and HDI 8 (hydroisomerizate), respectively of Example 1.
Figure 1:
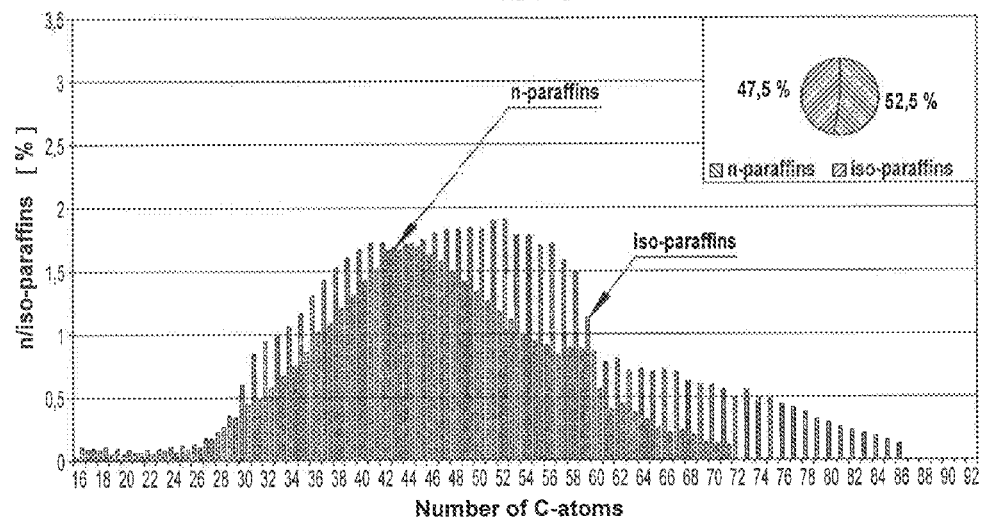

According to the process aspect of the invention, the microcrystalline paraffin can be prepared by catalytic isomerization as follows:

A. Use of FT paraffin as starting material
  a) having a carbon chain length in the range from $C_{20}$ to $C_{105}$,
  b) preferably having a solidification point in the range from 70 to 105° C., in particular about 70, 80, 95 or 105° C., in accordance with DIN ISO 2207,
  c) a penetration at 25° C. from 1 to 15,
  d) a ratio of isoalkanes to n-alkanes from 1:5 to 1:11,
B. Use of a catalyst, preferably in the form of extrudates, spheres, pellets, granules or powders, suitably based on
  a) 0.1 to 2.0% by mass, in particular 0.4 to 1.0% by mass, based on the catalyst fired at 800° C., of hydrogenating metal of transition group eight, in particular platinum and
  b) a support material comprising a zeolite of the beta type in an amount up to 60-95% by mass, based on the combination of all components fired at 800° C.,
C. Use of a process temperature above 200° C., in particular from 220 to 270° C.,
D. Use of a pressure from 0.5 to 20.0 MPa, preferably from 2 to 18 MPa, in particular from about 3 to 8 MPa, in the presence of hydrogen and a ratio of hydrogen to FT paraffin from 100:1 to 2000:1, in particular about 250:1 to 600:1 standard $m^3/m^3$,
E. A catalyst loading with FT paraffin in the range from 0.1 to 2.0 v/v·h (volume of FT paraffin per volume of catalyst over a period of one hour), in particular 0.2 to 0.8 v/v·h.

In general, the catalyst fills the reactor volume virtually completely, so that it is also possible to speak of the reactor volume instead of the catalyst volume.

The yield of the in each case solid hydroisomerizates is >90% by mass, in many cases between 90 and 96% by mass, based on the respective FT paraffin used. With regard to low-melting alkanes, the hydroisomerizates obtained still contain up to 5% (in general from 2 to 3%) of alkanes having carbon chain lengths of $<=C_{22}$. These alkanes can be separated off without problems by stripping with steam under reduced pressure.

A catalyst which can convert solid Fischer-Tropsch paraffin selectively into microcrystalline paraffins in a single process step is used.

The catalyst comprises a combination of
  60 to 95% by mass of zeolite of the beta type, based on the combination of all components fired at 800° C.,
  from 5 to 39.8% by mass of a high-surface-area gamma-aluminum oxide, calculated as $Al_2O_3$ and based on the combination of all components fired at 800°,
  and one or more metals of transition group 8 of ? the Periodic Table of the Elements (PTE), in particular platinum, in amounts from 0.2 to 2.0% by mass, based on the combination of all components fired at 800° C.,
and preferably consists of this, with the metal or plurality of metals of transition group 8 of the PTE, in particular platinum, being attached to the aluminum oxide.

A preferred catalyst composition for preparing microcrystalline paraffins from Fischer-Tropsch paraffins, in particular one having from about 20 to 105 carbon atoms, comprises
  from 75 to 90% by mass of zeolite of the beta type, based on the combination of all components fired at 800° C.,
  10 to 25% by mass of a high-surface-area gamma-aluminum oxide, calculated as $Al_2O_3$ and based on the combination of all components fired at 800° C.,
  and one or more metals of transition group 8 of the Periodic Table of the Elements (PTE), in particular platinum, in amounts from 0.4 to 1.0% by mass, based on the combination of all components fired at 800° C.,
with the metal or the plurality of metals of transition group 8 of the Periodic Table of the PTE, in particular platinum, being attached to the aluminum oxide. The catalyst preferably consists of these abovementioned components in the abovementioned mass ratios.

The high-surface-area gamma-aluminum oxide has a specific surface area of 15-350 $m^2/g$, based on $\gamma-Al_2O_3$.

The combination of all catalyst components fired at 800° C. is free of water and ammonium.

The catalyst is preferably produced by mixing 60 to 95% by mass, in particular 75 to 90% by mass, based on the combination of all components fired at 800° C., of a preferably pulverulent zeolite of the beta type (BEA type as described by W. M. Einer, H. H Olson & Ch. Bärlocher: Atlas of zeolite structure types, fourth ed., Elsevier London, Boston, Singapore, Sydney, Toronto, Wellington 1996),
  having an $SiO_2:Al_2O_3$ molar ratio from 19.3:1 to 100:1
  and a residue alkali content of not more than 0.05% by mass (based on zeolite calcined at 800° C.)
with 5 to 39.8% by mass, in particular 10 to 25% by mass, based on the combination of all components fired at 800° C., of a preferably pulverulent gamma-aluminum oxide precursor, in particular an aluminum hydroxide, preferably boehmite or pseudoboehmite, kneading the mixture with addition of water and acid as peptizing agent, extruding the mixture, firing the extrudates at temperatures from 80° C. to 200° C., in particular from 100° C. to 200° C., and impregnating the shaped bodies obtained with a compound of a metal or a plurality of metals of transition group 8 of the PTE, in particular platinum, in which the noble metal is present in anionic form and subsequently thermally after-treating, in particular drying and firing, the impregnated extrudates in air, so that 0.2 to 2% by mass of noble metal, based on the combination fired at 800° C., are present, and reducing the metal or metals of transition group 8 of the PTE, in particular platinum, to the metal by means of flowing hydrogen at elevated temperature.

This gives shaped catalyst bodies which can be employed in a heterogeneous process, in which the catalyst is preferably used as a fixed bed and the liquefied wax together with hydrogen is passed over it at temperatures of preferably from 200 to 270° C. in trickle phase mode. This catalyst combination achieves an activity in the isomerization which is sufficiently high for a Fischer-Tropsch paraffin which is solid at normal ambient temperature to be able to be used directly and a microcrystalline wax to be obtained in a single step. The properties of the microcrystalline wax can even be varied to some extent by choice of suitable reaction parameters.

Beta-zeolite is a commercially available product. It is preferably used according to the invention as crystalline aluminosilicate powder having the composition $Na_n[Al_nSi_{64-n}O_{128}]$ with n<7. In place of aluminum, boron or gallium can also be inserted isomorphously into the three-dimensional silicate structure. As a result of its high $SiO_2$ content, it can also be exposed to an acid medium without losing its crystalline structure, although part of the aluminum tetrahedra can be removed from the crystalline lattice. The beta-zeolite is preferably used as a fine powder having a particle size of, in particular, 0.5 to about 200 μm, measured by means of laser particle size analyzer. The zeolite has pores having diameters from about 0.5 to 0.8 nm. The 12-membered ring openings in the structure have a width of 0.55 nm in the [001] direction and a width of 0.64 or 0.76 nm in the [100] direction of the crystal lattice. As a result of these dimensions of the openings, the long, straight-chain paraffins are obviously able, at least to some extent, to enter into the internal structure of the zeolite with its acidic sites.

For the catalyst to be particularly effective in the isomerization, the alkali cations still present after the synthesis can be replaced as quantitatively as possible by protons. The replacement of the alkali cations by protons is carried out by methods known per se, for example by exchange with water-soluble ammonium salts and subsequent calcination at 500° C. The introduction of protons can also be carried out directly using dilute acids. After the calcination, the zeolites are in the Brönstedt or or Lewis acid form (acidic sites) which is active for carbonium ion reactions.

In the production of the catalyst, the zeolite is, in a preferred embodiment, in particular used as powder together with a γ-aluminum oxide A100H which serves simultaneously as binder for the zeolite and as support for a hydrogenation metal component, or comprises these in substantial proportions. The two powders are combined with one another and, simultaneously or afterward, dilute acid, for example mineral acid, preferably nitric acid, or organic acid, e.g. formic or acetic acid, as peptizing agent and sufficient water for a shapeable, plasticized mass to be formed on intensive working of the mass by kneading are added. To increase the plasticity, small amounts of up to about 5% by mass, based on the powder substances, of plasticizers, in particular organic auxiliaries, e.g. water-soluble cellulose ethers, are added in a preferred embodiment. This mass is extruded through nozzles, for example by means of a screw extruder, as a result of which shaped bodies in extrudate form having a chosen diameter and profile are formed. The extrudates are subsequently dried at temperatures from 80° C. to 200° C., in particular from 100° C. to 200° C., if desired broken to a particular length and treated thermally, in particular calcined, at temperatures from about 400° C. to 600° C., in a further step, so that all or virtually all organic constituents, water and any nitrate and ammonium ions are driven off from the shaped bodies.

On calcination at temperatures above about 350° C., the aluminum oxide precursor is converted into gamma-aluminum oxide which has a specific surface area of 150 to 350 $m^2/g$, based on $Al_2O_3$, and a pore volume from 0.3 to about 1.0 $cm^3/g$, based on $Al_2O_3$. The pores of the aluminum oxide preferably have diameters from 3 to 59 nm, making the aluminum oxide capable of taking up large molecules and transporting them to the zeolite crystals.

The calcined shaped bodies are impregnated with a solution containing the compound of the metal or metals of transition group 8 of the PTE, in particular of platinum. Particularly useful compounds for this purpose are $H_2[PtCl_6]$ and $H_2[PdCl_4]$. However, other suitable compounds in which the noble metals are present in anionic form can also be used. The compounds of the noble metals are, in a preferred embodiment, advantageously used in aqueous solution. The concentration of the noble metals in the solution is advantageously set so that the desired final concentration of these in the catalyst is established after uptake of the solution so as to simply fill the pores of the shaped bodies with the solution.

After impregnation of the shaped bodies with the solution of the noble metal compounds, the shaped bodies are preferably dried in an apparatus in order to remove water. The shaped bodies are subsequently fired in a stream of dry air, with the volatile compounds becoming liberated being carried away in the offgas. Nitrous gases formed may have to be destroyed.

The noble metals are then present as finely dispersed metalloxy, in particular platinum-oxy, compounds, while the zeolite crystals themselves do not contain any hydrogenation metal component. Before being used, the catalyst is reduced in a hydrogen-containing gas stream, in particular heated to temperatures from 100 to 480° C., to deposit the noble metal in finely divided metallic form on the aluminum oxide. The metal agglomerates are advantageously and in a preferred embodiment of the invention then present in such a form that at least 30% and at most about 70% of all metal atoms are capable of adsorbing a CO molecule.

The metal components function as hydrogenation-active constituents of the catalyst which are able to activate the long-chain paraffins to form carbonium ions. The latter react at the acidic sites in the catalyst so as to displace $CH_3$ groups on the long chains. After the transformation, paraffins which are singly methyl group branched primarily in the 2-, 3-, 4- and/or 5-position on the carbon chain emerge from the zeolitic pore openings. The catalyst can, for example, be used in the form of extrudates, cylinders, granules, spheres, pellets or powder.

The catalyst is preferably used in the presence of hydrogen at an $H_2$ partial pressure from 5 to 180 bar.

The catalyst is also preferably used at an $H_2$:feed ratio from 100:1 to 2000:1 standard $m^3/m^3$ of feed.

The catalyst is also preferably used at a loading from 0.1 to 1 volumes of feed/volumes of catalyst and hour.

The catalyst is also preferably used at a temperature from 200° to 270°.

The catalyst can also be used in the form of small particles suspended in the feed at temperatures from preferably 200° C. to 270° C. and elevated pressure in the presence of hydrogen in order to convert Fischer-Tropsch paraffin into microcrystalline wax. Any light constituents occurring can be driven off by means of steam distillation (stripping).

The catalyst is advantageously installed as a fixed bed in a reactor through which the feed together with hydrogen is allowed to flow slowly at temperatures from preferably 200° C. to 270° C. The catalyst can be used in a continuous, semicontinuous or batchwise mode of operation.

The catalyst is illustrated by means of the following example.

EXAMPLE

Production of a Catalyst 300 g of commercially available beta-zeolite having an $SiO_2$:$Al_2O_3$ molar ratio of 23.3 in the metal cation-free form (alkali content less than 0.05% by mass, based on zeolite calcined at 800° C.) as powder having a particle size from 0.5 to about 50 μm, 62.8 g of commercially available aluminum oxide hydroxide as fine powder and 8.4 g of water-soluble cellulose ether are intensively mixed with one another. 30 ml of dilute nitric acid containing 128 g of $HNO_3$/l and 350 ml of deionized water are then added and the mixture is kneaded intensively for one hour. This gives a shapeable, kneadable mass. The mass obtained in this way is extruded by means of a screw extruder through nozzles having cylindrical openings with a diameter of 1.5 mm, so that rod-shaped extrudates are formed. These are dried at 120° C. for 6 hours in a drying oven. The shaped bodies are broken to a length of 3-5 mm and calcined at 550° C. in a thin layer on a metal sheet for three hours in an electric muffle furnace through which air was slowly passed. Solid shaped bodies having a bulk density of 400 g/l are obtained.

The amount of water which can be taken up by the shaped bodies, which corresponds to the pore volume, is determined at room temperature (=110% based on the mass of catalyst). A solution of 1.636 g of $H_2PtCl_6$ in 242 ml of water is sprayed onto 220 g of the shaped bodies while the bodies are kept in motion. After the solution has been allowed to act on the shaped bodies for 10 minutes, the shaped bodies are partly dried while being kept in motion until the major part of the liquid has been vaporized and the individual shaped bodies no longer stick to one another. The impregnated shaped bodies are then dried at 120° C. in air in a drying oven. The dried shaped bodies are heated at 100° C./h to 450° C. in a stream of dry air in a vertical oven and maintained at 450° C. for one hour.

The shaped bodies are subsequently cooled to ambient temperature in the oven, the stream of air is replaced by pure nitrogen until the oxygen content in the out-flowing gas is less than 0.5% by volume and there is then change-over from nitrogen to hydrogen. The oven is once again heated at 100° C./h to 450° C. and the catalyst is treated, i.e. reduced, at this temperature in the stream of hydrogen for three hours. The catalyst is then allowed to cool in a stream of nitrogen and can then be taken out. The resulting catalyst A according to the invention is stable in air. The platinum content is 0.8% by mass, based on the combination of all components fired at 800° C.

Catalytic Test

The catalyst A produced above was comminuted to a particle size of 160-315 μm and 4 g of this comminuted catalyst were stirred into 180 g of a Fischer-Tropsch paraffin ("feed") at a temperature of 120° C. The mixture was placed in an autoclave. After the autoclave had been closed, it was pressurized with 50 bar of hydrogen and the mixture was heated to 250° C. whilst stirring and treated further for seven hours whilst stirring. The autoclave was then cooled to 120° C. again, and the product was taken from the autoclave, the catalyst was separated off and examined. The product data were compared with those of the feed (see table).

TABLE

Data for the feed and the hydroisomerizate

| | Feed | Hydroisomerizate |
|---|---|---|
| Number of C atoms (>90%) | 30 to 100 | About 25 to 100 |
| Solidification point in ° C. | 97 | 86.5 |
| Enthalpy of fusion ΔH | >200 | 125 |
| Penetration at 25° C. | 1-2 | 42 |
| Viscosity at 120° C. in cSt | ~12 | 15.4 |
| Isomer proportion in % by mass | ~12 | 47 |
| <C 22 in % by weight | 0 | 2-3 |

The hydroisomerizate displays properties which are distinctly different from the starting material and correspond to a microcrystalline wax. The proportion of the i-paraffins is considerably increased compared to the feed.

The catalytic hydroisomerization of the FT paraffins is preferably carried out continuously in a flow reactor using a fixed-bed catalyst, in particular in the form of extrudates, spheres or pellets. If the reactor is, as is preferred, aligned vertically, the flow through it can be either from the top downward or from the bottom upward. However, the process can also be carried out non-continuously or semicontinuously in, for example, a stirring autoclave in a batch process in which the catalyst is present in a permeable mesh or is finely dispersed as granules or powder in the FT paraffin. The process parameters of the continuous process and the batchwise process are identical.

The solid microcrystalline paraffins obtained according to the invention have the following properties:

Compared to the FT paraffins used, they have somewhat lower solidification points and comprise not only n-alkanes but also a high proportion by weight of isoalkanes, in particular a higher proportion by weight of isoalkanes than of n-alkanes. The proportion of n-alkanes or isoalkanes is determined by gas chromatography. The increased degree of isomerization achieved by means of the hydroisomerization is reflected in increased penetration values, a reduced degree of crystallization and a reduced enthalpy of fusion. The products were solid, white, opaque and of a sticky consistency. They were in each case solid at ambient temperature (20° C.).

The degree of crystallization is determined by X-ray diffraction analysis. It indicates the proportion of crystalline material in the product obtained as a ratio to the proportion of amorphous material. The amorphous materials lead to different diffraction of the X-rays than the crystalline materials. The needle penetration at 25° C. of the products according to the invention is in the range from 20 to 100, measured in accordance with DIN 51579.

The proportion of crystalline material is, in particular, reduced as follows: while a proportion of crystalline material in the range from 60 to 75% is present in the starting material, the proportion observed in the hydroisomerizate is from 30 to 45%, in particular in the range from 35 to 40%. This proportion of crystalline material is accordingly halfway between that of microcrystalline paraffins based on petroleum and that of the starting material, viz. the FT paraffins. The proportion of crystalline material in these synthetic microparaffins therefore also closes a gap in the use properties of such products, since the physical and materials properties of such products are generally functions of the crystallinity.

The proportions of crystalline and amorphous materials as determined by the abovementioned X-ray diffraction analysis are in each case reported in percent by mass.

The microcrystalline paraffins prepared by catalytic hydroisomerization can also be deoiled by means of a solvent.

However, this does not imply that the hydroisomerization products described have a content of oily components in the normal sense. However, short-chain n-alkanes and isoalkanes are removed. When a solvent mixture of dichloroethane:toluene in a volume ratio of 95:5 and a product:solvent ratio of 1:3.6 are used at 22° C., a deoiled microcrystalline paraffin is obtained in a yield from 80 to 90% by weight, based on the hydroisomerizate used. It has the following properties:

needle penetration: from $1\times10^{-1}$ to $7\times10^{-1}$ mm, in particular $3\times10^{-1}$ to $6\times10^{-1}$ mm, determined in accordance with DIN 51579, MBK-soluble material: 1.0 to 2% by weight, in particular 1.2 to 1.6% by weight, determined in accordance with ASTM D 721/87 modified so as to use MIBK, solidification point: about 60 to about 95° C., in particular 70 to 85° C., determined in accordance with DIN ISO 2207.

Removal of the short-chain material thus gives a very hard product, based on comparison with the grades obtained from petroleum, from the medium-hard product. The deoiled hydroisomerizate is then comparable with the hardest grades obtained from petroleum.

Owing to its properties, the microcrystalline hydroisomerizate prepared according to the invention and the corresponding deoiled microcrystalline hydroisomerizate can be used like a microwax (see introduction). In particular, the hydroisomerizate obtained can also be oxidized. The oxidation products obtained can differ in their melting range and degree of oxidation and can be used, in particular, as base products for corrosion protection products and as products for protecting hollow spaces in and the underside of motor vehicles. They are also used in emulsions as cleaning products and release agents and as additives in printing inks and carbon paper compositions.

The acid and ester groups which are randomly distributed over the hydrocarbon chains can be reacted with inorganic or organic bases to produce formulations which are dispersible in water (emulsifiable waxes) and lead to products having very good adhesion to metals.

Further application areas are the production of impregnation, coating and lamination waxes for the packaging and textile industries, heat sealing compounds and hot melt adhesives, as blend components in candles and other wax products, in wax mixtures for drawing chalk, floor care products and automobile care products and for dental technology and pyrochemistry.

They are also constituents of light-protection waxes for the tire industry, electrical insulation materials, framework and modeling waxes for the fine casting industry and wax formulations for explosives, munitions and propellant technology.

Furthermore, such products are suitable as release agents in the pressing of chipboard, particleboard and fiberboard, in the production of ceramic parts and, owing to their retention capacity, for the production of solvent-containing cleaners, grinding and polishing pastes and as matting agents for surface coatings.

These products can also be used for formulating adhesive waxes, cheese waxes, cosmetic preparations, chewing gum bases, casting and cable insulation compositions, sprayable pesticides, vaselines, artificial firewood, lubricants and hot melt adhesives.

The synthetic microwaxes are foodsafe. Testing is carried out in accordance with FDA, §175.250.

The invention will now be illustrated specifically by means of examples.

Example 1

An FT paraffin having a solidification point of 97° C. was catalytically isomerized by means of hydrogen at a pressure of 5 MPa (50 bar), a temperature of 270° C. and a v/vh ratio of 0.3 in a flow reactor. The hydroisomerization occurring is evidenced by the data in table 1.

The catalyst comprised 0.8% by mass of platinum on β-zeolite and an $SiO_2$ to $Al_2O_3$ molar ratio of 23:1 and an aluminum oxide having a large surface area. The catalyst was in acid form. It contained less than 0.02% of alkali oxide on a dry basis.

The hydroisomerizate obtained was solid, white-opaque, odorless, slightly sticky and thus differed significantly from the hard-brittle starting material. The isoalkane content had been increased by a factor of about 5, which is reflected in the increased penetration value, the reduced proportion of crystalline material and the reduced enthalpy of fusion. The synthetic, microcrystalline paraffin prepared in this way is in terms of its properties between a plastic petroleum-based microwax and a hard petroleum-based microwax. The hydroisomerizate is thus a paraffin which has a pronounced microcrystalline structure and whose carbon chain length distribution of 23 to 91 carbon atoms corresponds approximately to that of the starting material with 27 to 95 carbon atoms but shifted slightly to shorter chain lengths. The chain lengths were determined by gas chromatography; a corresponding gas chromatogram is attached as FIG. 1.

Example 2

An FT paraffin having a solidification point of 71.5° C. was catalytically isomerized under a hydrogen pressure of 5 MPa (50 bar) at a temperature of 250° C. in an autoclave. The structural transformation which has occurred is evidenced by the data in the table.

The same catalyst as in example 1 was used.

The hydroisomerizate obtained was solid, white-opaque and odorless and also paste-like and slightly sticky. The isoalkane content was increased by a factor of about 5. The high degree of isomerization is reflected in the significantly increased penetration value, the reduced proportion of crystalline material and the reduced enthalpy of fusion. The microcrystalline paraffin obtained in this way has a similar but somewhat shorter carbon chain length than the FT paraffin, which is clearly indicated by the number of carbon atoms: 23 to 42 in the case of the hydroisomerizate and 25 to 48 in the case of the FT paraffin. The synthetic microcrystalline paraffin prepared in this way is comparable in terms of its properties to a soft plastic microcrystalline paraffin obtained from-petroleum.

Examples 1 and 2 show that the FT paraffins, which consist predominantly of n-alkanes and have a finely crystalline structure and a hard-brittle consistency, were converted by the process of the invention into nonfluid, paste-like or solid paraffins which have lower melting points than the starting materials. These paraffins have a high content of branched alkanes and consequently are distinguished by a microcrystalline structure with a significantly reduced degree of crystallization (compared to the starting material) and a plastic to slightly sticky consistency. The branched alkanes are predominantly methylalkanes, with the methyl groups preferably being located in the 2-, 3-, 4- or 5-position. Multiply methyl-branched alkanes were also formed to a small extent.

The results of examples 1 and 2, and also the properties of the starting material for comparison, are shown in the accompanying table 1.

A gas chromatogram corresponding to example 2 is shown in FIG. 2.

Example 3

The starting material of example 2 was then isomerized in a flow reactor, once again using the same catalyst, to give a hydroisomerizate having somewhat different but comparable properties (cf. also table 1 in this regard) as in the autoclave experiment (example 2), at a significantly reduced process temperature of 220° C. A reactor experiment is significantly closer to industrial implementation of the hydroisomerization than is an autoclave experiment. The possibility of reducing the process temperature compared to the autoclave experiment which has thus been demonstrated allows the same-to be expected in the case of example 1 when carried out industrially.

The reduction in the process temperature is also associated with the considerable advantage that the cracking reaction which competes with such a hydroisomerization is substantially suppressed (cf. FIGS. 1 to 3).

A gas chromatogram corresponding to example 3 is attached as FIG. 3.

In contrast to the microcrystalline paraffins obtained from petroleum, the fully synthetic microcrystalline paraffins prepared by means of the hydroisomerization according to the invention contain no highly branched isoalkanes, no cyclic hydrocarbons (naphthenes) and, in particular, no aromatics and sulfur compounds. They thus correspond to the highest purity requirements for 7 microcrystalline paraffins and are thus highly suitable for use in the cosmetic and pharmaceutical industry and for packaging and preservation in the food industry.

TABLE 1

Properties of starting materials and reaction products

|  | Unit | Measurement method | Example 1 | | Example 2 | | Example 3 | |
| --- | --- | --- | --- | --- | --- | --- | --- | --- |
|  |  |  | FT paraffin (H8) | Hydro-isomerizate (HDI-8) | FT paraffin (FT 70) | Hydro-isomerizate (HDI 70-A) | FT paraffin (FT70) | Hydro-isomerizate (HDI 70-R) |
| Solidification point | ° C. | DIN ISO 2207 | 97.0 | 86.5 | 71.5 | 61.5 | 71.5 | 64.5 |
| Penetration N at 25° C. | 0.1 mm | DIN 51579 | 2 | 42 | 13 | 98 | 13 | 79 |
| Enthalpy of fusion | J/g | ASTM D4419 | 221 | 127 | 195 | 120 | 195 | 142 |
| Proportion of crystalline material | % by mass | X-ray diffraction analysis | 70.7 | 43.5 | 62.4 | 38.8 | 62.4 | 41.2 |
| Isoalkanes | % | Gas chromatography | 12 | 47 | 9 | 47 | 9 | 40 |
| MIBK-soluble material | % by mass | ASTM D721-87 (modified) | 0.66 | 14.6 | 0.4 | 23.1 | 0.4 | 15.0 |
| Viscosity (100° C.) | cSt |  | 12 (120° C.) | 15.4 (120° C.) | 6.5 | 5.2 | 6.5 | 5.1 |

We claim:

1. A process for catalytically hydroisomerizing FT (Fischer-Tropsch) $C_{20-105}$ paraffins, comprising contacting the FT $C_{20-105}$ paraffins with a catalyst, at a temperature ranging from 200° C. to 270° C., wherein the FT paraffins are in a liquid phase, and at a pressure ranging from 2 to 20 MPa, in the presence of hydrogen, to produce a microcrystalline paraffin; wherein the catalyst comprises 60 to 95% by mass of zeolite of the beta type, based on the combination of all components fired at 800° C., 5 to 39.8% by mass of gamma-aluminum oxide having a specific surface area of 150-350 $m^2/g$, calculated as $Al_2O_3$ and based on the combination of all components fired at 800° C., and one or more metals of transition group 8 of the periodic table, in an amount of 0.1 to 2.0% by mass, based on the combination of all components fired at 800° C., the one or more transition group 8 metals being attached to the gamma-aluminum oxide; and wherein the catalyst is prepared by a process comprising the steps of:

(i) mixing 60 to 95% by mass, based on the combination of all components fired at 800° C., of a pulverulent zeolite of the beta type, having an $SiO_2$:$Al_2O_3$ molar ratio from 19.3:1 to 100:1, and a residue alkali content of not more than 0.05% by mass, based on zeolite calcined at 800° C., with 5 to 39.8%, based on the combination of all components fired at 800° C., of a pulverulent aluminum oxide, to form a mixture, (ii) kneading the mixture with addition of water and acid as peptizing agents, (iii) extruding the mixture to produce extrudates, (iv) drying and firing the extrudates at temperatures from 80° to 200° C. to produce shaped bodies, (v) impregnating the shaped bodies with a compound of a metal or a plurality of metals of transition group 8, in which the metal or a plurality of metals is present in anionic form, and (vi) reducing the compound of a metal or a plurality of metals of transition group 8, to metal form by contacting the shaped bodies with flowing hydrogen at elevated temperature.

2. The process according to claim 1, wherein the β-zeolite further comprises pores comprising a pore size between 0.50 and 0.80 nm.

3. The process according to claim 1, wherein the pressure is 3 to 8 Mpa.

4. The process according to claim 1, wherein the process is conducted at a temperature of 220° C. to 270° C.

5. The process according to claim 1, wherein the hydrogen is fed to the paraffin, in a feed ratio of hydrogen to FT paraffin from 100:1 to 2000:1 standard $m^3$ per $m^3$.

6. The process according to claim 1, wherein the hydrogen is fed to the paraffin, in a feed ratio of hydrogen to FT paraffin from 250:1 to 600:1 standard $m^3$ per $m^3$.

7. The process according claim 1, wherein the process is carried out at a loading from 0.1 to 2.0 v/vh.

8. The process according to claim 2, wherein the catalyst has a pore size between 0.55 to 0.76 nm.

9. The process according to claim 1, wherein the one or more metals of transition group 8 of the Periodic Table comprises platinum.

10. The process according to claim 9, wherein the platinum content of the catalyst is 0.2 to 2.0% by mass, based on a catalyst fired at 800° C.

11. The process according to claim 1, wherein the FT paraffins have a solidification point ranging from 70 to 105° C.

12. The process according to claim 1, wherein the microcrystalline paraffin is prepared from the FT paraffins in a single process step.

13. The process according claim 1, wherein the process is carried out at a loading from 0.2 to 0.8 v/vh.

14. The process according to claim 9, wherein the platinum content of the catalyst is 0.4 to 1.0% by mass, based on a catalyst fired at 800° C.

15. The process according to claim 11, wherein the FT paraffins have solidification points of 70, 80, 95 or 105° C.

16. The process according to claim 12, wherein the microcrystalline paraffins are prepared from the FT paraffins in a single process step, with removal of the short chain constituents.

17. A process for preparing a microcrystalline paraffin comprising;
(a) preparing a catalyst by a method comprising the steps of
(i) mixing 60 to 95% by mass, based on the combination of all components fired at 800° C., of a pulverulent zeolite of the beta type, having an $SiO_2:Al_2O_3$ molar ratio from 19.3:1 to 100:1, and a residual alkali content of not more than 0.05% by mass, based on zeolite calcined at 800° C., with 5 to 39.8%, based on the combination of all components fired at 800° C., of a pulverulent aluminum oxide, to form a mixture,
(ii) kneading the mixture with addition of water and acid as peptizing agents,
(iii) extruding the mixture to produce extrudates,
(iv) drying and firing the extrudates at temperatures from 80° to 200° C. to produce shaped bodies,
(v) impregnating the shaped bodies with a compound of a metal or a plurality of metals of transition group 8, in which the metal or a plurality of metals is present in anionic form, and
(vi) reducing the compound of a metal or a plurality of metals of transition group 8, to metal form by contacting the shaped bodies with flowing hydrogen at elevated temperature and
wherein the produced catalyst comprises 60 to 95% by mass of zeolite of the beta type, based on the combination of all components fired at 800° C., 5 to 39.8% by mass of gamma-aluminum oxide having a specific surface area of 150-350 $m^2/g$, calculated as $Al_2O_3$ and based on the combination of all components fired at 800° C., and one or more metals of transition group 8 of the periodic table, in an amount of 0.1 to 2.0% by mass, based on the combination of all components fired at 800° C., the one or more transition group 8 metals being attached to the gamma-aluminum oxide; and
(b) contacting FT $C_{20-105}$ paraffins with the catalyst of (a), at a temperature ranging from 200° C. to 270° C., wherein the FT $C_{20-105}$ paraffins are in a liquid phase, and at a pressure ranging from 2 to 20 MPa, in the presence of hydrogen, to produce a microcrystalline paraffin.

* * * * *